(12) United States Patent
Jung

(10) Patent No.: US 9,239,318 B2
(45) Date of Patent: Jan. 19, 2016

(54) SPECTROSCOPIC SAMPLE INSPECTION FOR AUTOMATED CHROMATOGRAPHY

(75) Inventor: Moon Chul Jung, Arlington, MA (US)

(73) Assignee: Waters Technologies Corporation, Milford, MA (US)

( * ) Notice: Subject to any disclaimer, the term of this patent is extended or adjusted under 35 U.S.C. 154(b) by 133 days.

(21) Appl. No.: 13/980,972

(22) PCT Filed: Feb. 14, 2012

(86) PCT No.: PCT/US2012/024949
§ 371 (c)(1),
(2), (4) Date: Jul. 22, 2013

(87) PCT Pub. No.: WO2013/101262
PCT Pub. Date: Jul. 4, 2013

(65) Prior Publication Data
US 2013/0327129 A1    Dec. 12, 2013

Related U.S. Application Data

(60) Provisional application No. 61/447,190, filed on Feb. 28, 2011.

(51) Int. Cl.
*G01N 30/00* (2006.01)
*G01N 21/65* (2006.01)
(Continued)

(52) U.S. Cl.
CPC . *G01N 30/00* (2013.01); *G01J 3/46* (2013.01); *G01N 21/65* (2013.01); *G01N 30/74* (2013.01)

(58) Field of Classification Search
CPC .............. Y10T 436/255; Y10T 436/25; Y10T 436/25375; G01N 2030/009; G01N 1/28; G01N 1/38; G01N 1/40; G01N 1/405; G01N 1/44; G01N 2001/4061; G01N 2035/00128; G01N 21/35; G01N 21/3581; G01N 21/359; G01N 21/31; G06T 7/0012; G06T 2207/30024; G06T 2207/30072
See application file for complete search history.

(56) References Cited

U.S. PATENT DOCUMENTS 3,966,410 A   6/1976   Jahnsen
5,858,178 A   1/1999   Lautenschlager
(Continued)

OTHER PUBLICATIONS

International Search Report & Written Opinion of the International Searching Authority (US) in related international patent application No. PCT/US2012/024949, mailed on May 30, 2012; 10 pages.
(Continued)

*Primary Examiner* — Sally Merkling
(74) *Attorney, Agent, or Firm* — Schmeiser, Olsen & Watts LLP; William G Guerin

(57) ABSTRACT

A method and a system for generating an extraction sample from a dried sample spot. The method includes acquiring a spectroscopic image of an analyte in the spot. The spectroscopic image includes information on a spatial distribution of the analyte. A region of the spot to be extracted is determined from the spectroscopic image and an extraction sample is generated from the determined region. In other embodiments, the method and system are based on acquiring a spectroscopic measurement of an analyte in the dried sample spot, determining a quantity of the analyte in the spot based on the spectroscopic measurement and determining a volume of an extraction solvent for creating an extraction sample from the spot. The determined volume is based on the determined quantity of the analyte and a detection characteristic of an analytical measurement system. In other embodiments, the method is applied to solid samples.

26 Claims, 6 Drawing Sheets

(51) Int. Cl.
*G01N 30/74* (2006.01)
*G01J 3/46* (2006.01)

(56) References Cited

U.S. PATENT DOCUMENTS

| | | | |
|---|---|---|---|
| 2003/0098248 A1* | 5/2003 | Vogel et al. | 205/777.5 |
| 2004/0009610 A1 | 1/2004 | Schabron et al. | |
| 2010/0136609 A1* | 6/2010 | Clay et al. | 435/34 |
| 2011/0129940 A1 | 6/2011 | Gijlers et al. | |
| 2012/0082362 A1* | 4/2012 | Diem et al. | 382/133 |

OTHER PUBLICATIONS

Abu-Rabie, Paul and Neil Spooner, "Direct Quantitative Bioanalysis of Drugs in Dried Blood Spot Samples Using a Thin-Layer Chromatography Mass Spectrometer Interface", Analytical Chemistry, vol. 81, No. 24, Dec. 15, 2009; pp. 10275-10284.

Prolab Instruments GmbH, "scap System DBS: Dried Blood Spot Automated sample extraction platform for online LC-MS/MS bioanalysis", accessed Nov. 3, 2010, Reinach, Switzerland; 4 pages.

International Preliminary Report on Patentability in related International Patent Application No. PCT/US12/04949, mailed Sep. 12, 2013, 8 pages.

* cited by examiner

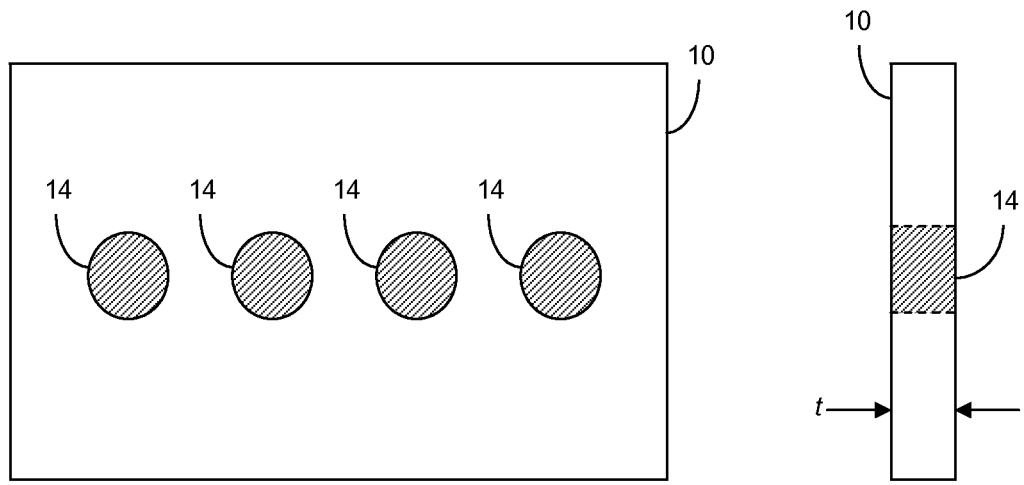
FIG. 1A                    FIG. 1B
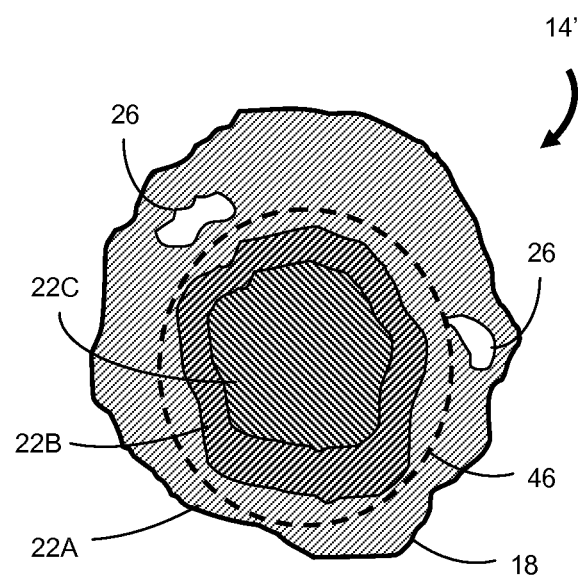
FIG. 2

SPECTROSCOPIC SAMPLE INSPECTION FOR AUTOMATED CHROMATOGRAPHY

RELATED APPLICATION

This application claims the benefit of the earlier filing date of U.S. Provisional Patent Application Ser. No. 61/447,190, filed Feb. 28, 2011 and titled "Spectroscopic Sample Inspection for Automated Chromatography," the entirety of which is incorporated herein by reference.

FIELD OF THE INVENTION

The invention relates generally to methods and systems for pre-screening dried sample spots prior to measurement by analytical equipment. More particularly, the invention relates to spectroscopic sample inspection of a dried sample spot to generate an estimate of a target analyte concentration and to determine a preferred region of the dried sample for extraction.

BACKGROUND

Dried blood spot (DBS) sampling offers advantages over venous blood sampling. For example, the small volume of blood in DBS samples accommodates collection in preclinical drug analysis studies using small animals such as mice and rats without sacrificing the subject animals. In addition, the small volume makes clinical collection more tolerable, especially for children and infants. A typical DBS carrier is in the form of a collection card manufactured from absorbent filter paper and adapted to hold a plurality of DBS samples. After blood is applied to the DBS card, the blood is allowed to dry for several hours. The resulting DBS is substantially inert. Advantageously, the small sample volume acquired for the DBS and the reduced sensitivity of the DBS to temperature make transporting DBS samples convenient and inexpensive. In addition, DBS samples can be stored for months without refrigeration and handled at room temperature in ambient atmospheric conditions over a moderate range of humidity.

The effort required at the analysis site to extract the DBS components from the DBS card and the variability in the measurement results are significant disadvantages when compared with conventional measurements performed using venous blood samples. The present invention successfully addresses these problems and provides additional advantages.

SUMMARY

In one aspect, the invention features a method of generating an extraction sample from a dried sample spot. The method includes acquiring a spectroscopic image of an analyte in a dried sample spot. The spectroscopic image includes information on a spatial distribution of the analyte in the dried sample spot. A region of the dried sample spot for extraction is determined from the spectroscopic image and an extraction sample is generated from the determined region. In some embodiments, the method is applied to a solid sample instead of a dried sample spot.

In another aspect, the invention features a system for generating an extraction sample from a dried sample spot. The system includes a spectroscopic measurement module, a processor, a first conduit, a second conduit and a positioning mechanism. The spectroscopic measurement module is configured to obtain a spectroscopic image of a dried sample spot on a sample carrier. The spectroscopic image includes information on a spatial distribution of an analyte in the dried sample spot. The processor is in communication with the spectroscopic measurement module to receive the spectroscopic image. The processor is configured to determine a region of the dried sample spot for extraction and to generate a position control signal responsive to the location of the determined region on the sample carrier. The first conduit has an outlet port to provide an extraction solvent and the second conduit has an inlet port to receive the extraction solvent. The positioning mechanism is in communication with the processor and is configured to position the outlet and inlet ports proximate to the determined region at the sample carrier in response to the position control signal. A solvent flows from the outlet port to the determined region of the dried sample spot and through the inlet port into the second conduit. The solvent in the second conduit comprises an extraction sample from the dried sample spot.

In another aspect, the invention features a method of generating an extraction sample from a dried sample spot. The method includes acquiring a spectroscopic measurement of an analyte in a dried sample spot. A quantity of the analyte in the dried sample spot is determined from the spectroscopic measurement and a volume of an extraction solvent to be used to create an extraction sample from the dried sample spot is determined based on the determined quantity of the analyte and a detection characteristic of an analytical measurement system. In some embodiments, the method is applied to a solid sample instead of a dried sample spot.

In still another aspect, the invention features a system for generating an extraction sample from a dried sample spot. The system includes a spectroscopic measurement module, a processor and a solvent management module. The spectroscopic measurement module is configured to generate spectroscopic data indicative of a quantity of an analyte in a dried sample spot. The processor is in communication with the spectroscopic measurement module and is configured to receive the spectroscopic data. The processor determines a volume of an extraction solvent for creating an extraction sample from the dried sample spot. The solvent management module is in communication with the processor and is configured to provide the determined volume of the extraction solvent at the dried sample spot.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

FIG. 1A and FIG. 1B are front and cross-sectional side views, respectively, of a DBS card.

FIG. 2 is a simplified illustration of an example of a DBS.

DETAILED DESCRIPTION

Figure 3:
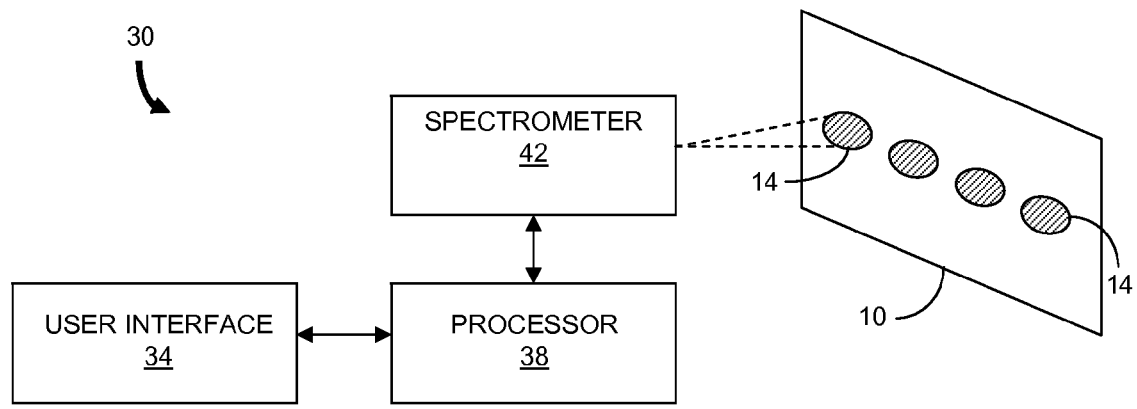
FIG. 3 is a block diagram of an embodiment of a system for determining a region for extracting a sample from a dried sample spot according to the invention.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

One disadvantage to DBS analysis is the effort required at the analysis site to extract the DBS components from the DBS card. Moreover, the variability in measurement results can be significant when compared to variations in results from measurements performed using venous blood samples. For typical DBS measurements, a DBS card is punched so that a single DBS to be analyzed is separated from the card as a small disk. Care is taken by the analyst during the punch process to ensure that the DBS card is accurately punched at the location of the DBS. The separated disk is placed into a solvent to extract the DBS components, including at least one analyte of interest. The particular solvent used for extraction is generally selected according to the analyte to be detected and quantified. The disk and solvent may be shaken or subjected to ultrasonic energy to improve the efficiency of the extraction process. After a sufficient time, the supernatant of the extraction is collected and used for testing. One potential disadvantage of the technique is that analyte concentration information available from the original blood sample can be lost in the extraction process. To address this problem, care can be taken when acquiring a sample from a subject so that a known volume of blood is used to generate the DBS. Knowledge of the volume of solvent used to extract the blood components from the DBS, the volume of the original blood sample used to create the DBS and the size of a disk separated from the DBS can be used to determine the analyte concentration in the original blood sample.

The manual process of punching DBS cards and the subsequent extraction of the DBS components from the disks requires significant time and is often labor intensive. An alternative process of online extraction can be used in which two extraction conduits are employed to extract the DBS components from the DBS card. In some online extraction processes, the first conduit is positioned at one side of the card at the position of a DBS and the second conduit is positioned at the opposite side of the card at the position of the same DBS.

In other online extraction processes, the first and second conduits are positioned on the same side of the card. The first conduit supplies the extraction solvent to the DBS. The second conduit receives the extraction solvent with the DBS components (i.e., the extraction sample). The second conduit supplies the extraction sample to analytical equipment so that the quantity of one or more analytes in the extraction sample can be determined.

The automated process of online extraction has disadvantages. The diameters of the extraction conduits are generally smaller than the diameter of the DBS thus difficulties can arise. For example, the analyte may not be homogeneously distributed in the DBS. More particularly, the spatial distribution of the analyte can vary significantly with location within the DBS and the concentration of the analyte near the edge of the DBS is often substantially less than the concentration in the central region. Thus the automated process can lose concentration information if the extraction conduits are not properly positioned relative to the DBS.

A digital imaging system can be used to acquire an image of the DBS. The image is processed to determine the center of the DBS and to avoid selection of a region of the card near the DBS that does not include sufficient sample. One problem with the visual image analysis technique is that the distribution of the analyte of interest in the DBS may not correspond accurately in position relative to the image of the DBS acquired by the camera. This problem is generally more pronounced when the analyte is a small molecule or if the analyte is significantly hydrophobic or hydrophilic, thus the distribution pattern of the analyte is different from that of blood matrix.

In other applications, dried samples of materials other than blood may be tested. For example, analytes in saliva, urine and other samples may be tested. Such dried sample spots are often not easily observable by camera as the sample may be more visually transparent than a DBS. Consequently, finding the optimal extraction spot is substantially more difficult.

The following description relates primarily to inspection and analysis of DBS samples in accordance with principles of the invention; however, it will be recognized that the methods and systems described herein can readily be adapted for dried sample spots of other types, such as saliva spots, serum spots and urine spots.

FIG. 1A is an illustration of a sample carrier 10 in the form of a DBS card that includes a number of DBSs 14. Each DBS 14 may include one or more analytes of interest to be detected by an analytical measurement system. Each DBS 14 extends partially into the card or through the thickness t of the card as shown in FIG. 1B. Although not shown, a holder or frame may be secured to at least a portion of the carrier 10 to enable convenient handling without contamination of the absorbent portions of the card that include the DBSs 14.

FIG. 2 is a simplified illustration of an example of a DBS 14' that has a nominal circular shape. The concentration of an analyte of interest is typically not homogeneously distributed but instead varies with position in the DBS 14'. Often the analyte has a higher concentration near the center of the DBS 14'. In some instances, the presence of the analyte is irregular such that there are small regions with little or no concentration of the analyte. The illustration shows an outline 18 of the DBS 14' that surrounds areas of light, moderate and heavy sample concentration 22A, 22B and 22C, respectively. Also visible are regions 26 of little or no sample concentration.

Although a digital image of the DBS 14' can be acquired and subsequently analyzed to determine the spatial characteristics of the spot, the distribution of the analyte of interest within the DBS 14' may not correspond accurately to the visible features or color content in the acquired image. For example, the red intensity at various locations within the image of the DBS 14' may not accurately correlate to the presence of the analyte of interest at those locations.

FIG. 3 is a block diagram of an embodiment of a system 30 for determining a region for extracting a sample from a dried sample spot such as a DBS 14. The system 30 includes a user interface (UI) module 34, a processor 38 and a spectroscopic measurement module (spectrometer) 42. The UI module 34 is in communication with the processor 38. As illustrated, the processor 38 is separate from and in bidirectional communication with the spectrometer 42. Input data from the UI module 34 are received by the processor 38 and used to generate or modify control signals for operation of the spectrometer 42. Measurement data from the spectrometer 42 are received by the processor 38 and may be presented to the user through the UI module 34 in graphical and textual formats. In one embodiment, the processor 38 includes components optimized for image processing. In other embodiments the processor 38 is integrated as a system component of the spectrometer 42. In some embodiments, at least one of the UI module 34 and the processor 38 is in communication with or integrated as a subsystem component of an analytical measurement system such as a high-performance liquid chromatography (HPLC) system, an ultra-performance liquid chromatography (UPLC) system or a mass spectrometer. In some embodiments, a first analytical measurement system, such as an HPLC or UPLC system, is coupled at its output to a mass spectrometer.

The system 30 is operated as a high-speed optical scanner to acquire spectroscopic data for the DBS 14. The spectroscopic data varies according to the illumination source and detector employed in the spectrometer 42. For example, the spectroscopic measurement can be a simple ultraviolet (UV) or visible spectrum measurement. Alternatively, the spectroscopic measurement can be based on Raman spectroscopy.

Many advantages are realized using spectroscopy measurement data. For example, each chemical compound, or analyte, has a unique spectrum, or "fingerprint", that can be used for identification. The magnitude of the spectrum data can be processed to obtain concentration information. Thus the system 30 enables a spectroscopic image of the DBS 14 to be acquired. The image includes information on the spatial distribution of one or more analytes of interest within the DBS 14. The spectroscopic image is effectively a two-dimensional chemical map that can be used to determine a preferred extraction region on the DBS carrier 10.

In other applications, transparent sample spots can be provided for analysis. By way of examples, transparent sample spots include spots formed by plasma, urine, saliva and cerebrospinal fluid samples. Spectroscopic images of such spots enable a better determination of the spatially-variant concentration of the samples and analytes within the dried sample spots.

In certain preferred embodiments, the spectrometer 42 is a Raman mapping module having a compact laser for a scanned illumination of the DBS 14. Such modules are commercially-available in small package formats, including benchtop and handheld packages. Embodiments utilizing Raman spectrometers are particularly sensitive to the presence of small molecules because Raman signals from small molecules are typically stronger than Raman signals from large molecules. Consequently, the background signal from the blood matrix, containing cells, proteins and lipids, is relatively unobtrusive. Moreover, sub-micron spatial resolution is achievable with some Raman spectrometers. Quantitative information provided by the Raman spectrometer can be used to estimate analyte concentration and to determine improved extraction parameters, including extraction solvent volume, to be used for sample generation for liquid chromatography.

Figure 4:
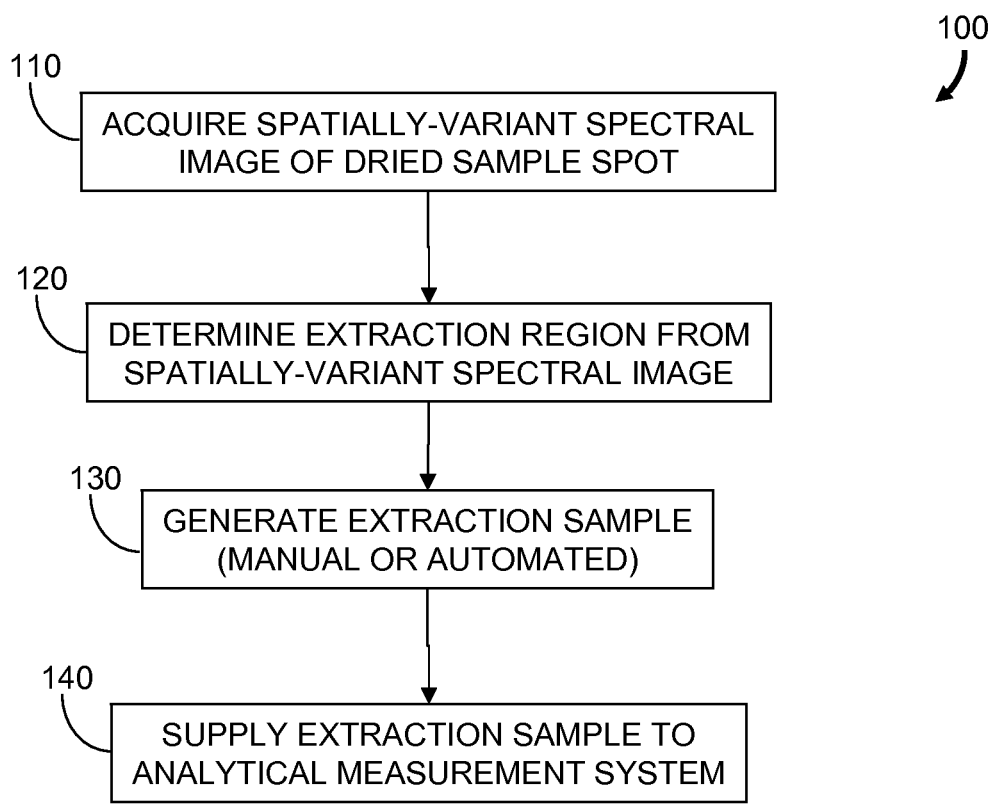
FIG. 4 is a flowchart representation of an embodiment of a method for generating an extraction sample from a dried sample spot according to the invention.

FIG. 4 is a flowchart representation of an embodiment of a method 100 for generating an extraction sample from a dried sample spot such as a DBS. Referring to FIG. 3 and FIG. 4, a spatially-variant spectroscopic image of an analyte in the dried sample spot 14 is acquired (step 110). The spectroscopic image from the spectrometer 42 is analyzed by the processor 38 to determine (step 120) a region within or about the spot 14 to use for extraction. As used herein, extraction means the process of acquiring some or all of the constituents of the DBS in a volume of extraction solvent to create an extraction sample. The determination of the region to be extracted is based on the spatial distribution of the analyte of interest as present in the spectroscopic image. The determination can be based on maximizing the analyte within a certain aperture, for example, as a disk of a predetermined diameter to be punched from the DBS card 10. The circular dashed line 46 in FIG. 2 is an example of how the punch location may be offset from the visual center of a DBS14'. Alternatively, the extraction region can be selected according to minimizing a variation of the analyte content across a predetermined aperture, for example, to avoid areas of substantial inhomogeneity. If the system 30 is to be used in an online extraction process, the aperture used for determining the extraction region can be based on the diameters of conduits used to flow an extraction solvent through the DBS 14 and card 10 in an automated manner as described below.

An extraction sample is generated (step 130) from the determined region of the dried sample spot. As described above, the extraction sample can be generated by a manual or automated punch process in which a portion of the carrier 10 is separated from the remainder of the carrier and placed in a solvent. Alternatively, the extraction sample can be generated according to the online process described above.

The extraction sample is subsequently provided (step 140) to analytical measurement equipment such as a HPLC system or an UPLC system to accurately determine the quantity of one or more analytes of interest in the dried sample spot.

Figure 5:
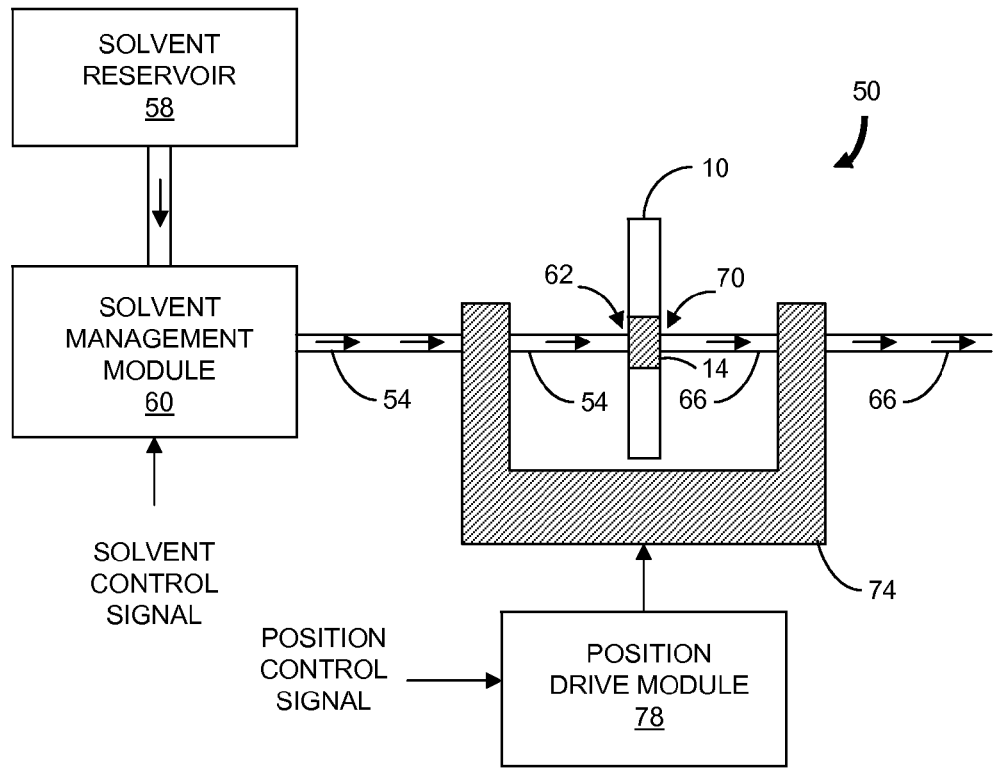
FIG. 5 is a block diagram of components for an embodiment of a system for automated online sample extraction from a dried sample spot according to the invention.

FIG. 5 is a block diagram of a portion of a system 50 for automated online sample extraction from a dried sample spot. The illustrated system components can be used in combination with the components of FIG. 3 to generate one or more extraction samples from a dried sample spot carrier.

The system 50 includes a supply conduit 54, such as tubing, to supply an extraction solvent held in a solvent reservoir 58. A solvent manager module 60 disposed between the solvent reservoir 58 and the supply conduit 54 controls the flow of the extraction solvent that exits the outlet port 62 of the supply conduit 54. A DBS card 10 or other dried sample spot carrier is secured in position by a card mount or support (not shown). An extraction conduit 66 is positioned on the opposite side of the DBS card 10 from the supply conduit 54. In alternative embodiments, the extraction conduit 66 is positioned close to the supply conduit 54 on the same side of the DBS card 10 or the supply conduit 54 also retrieves the extraction solvent from the DBS card so that an extraction conduit is not used. In the illustrated embodiment, the extraction conduit 66 has an inlet port 70 to receive the extraction solvent after passing through the DBS card 10. During operation, the inlet port 70 is aligned with the outlet port 62 so that the ends of the conduits 54 and 66 near the DBS card 10 are in fluidic communication with each other through the DBS 14. Although not a requirement, the diameters of the ports 62 and 70 can be smaller than the nominal diameter of the DBS 14.

The system 50 also includes a positioning mechanism 74 and position drive module 78 to position the outlet and inlet ports 62 and 70 relative to the DBS 14. In various embodiments, the positioning mechanism 74 includes one or more linear translators and/or rotary drives. The position drive module 78 responds to at least one position control signal from the processor 38 (see FIG. 3) and controls the positioning mechanism 74 so that the inlet and outlet ports 62 and 70 are properly positioned with respect to a particular DBS 14 on the DBS card 10. By way of an example, the ports 62 and 70 can be aligned to extract from a predetermined region as shown by the circular dashed line 46 of FIG. 2.

Figure 6:
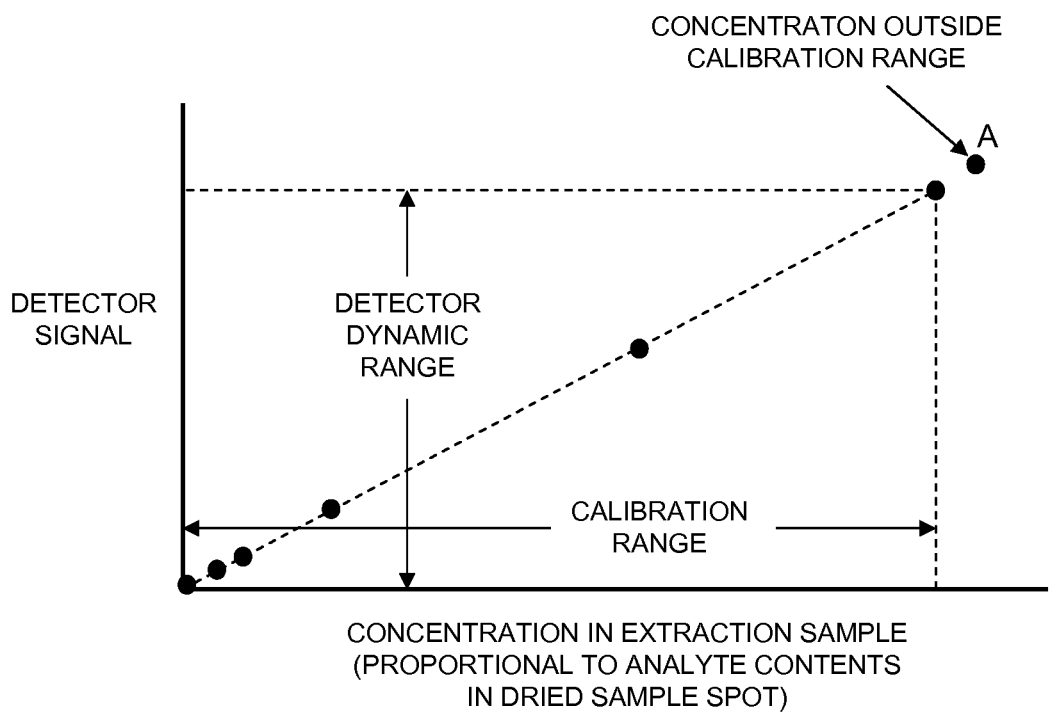
FIG. 6 is a graphical representation of a calibration of a detector signal as a function of analyte content in a sample.

Generally, to achieve the proper concentration for a reconstituted sample, the volume of the original sample used to generate the dried sample spot is known and the extraction solvent applied to the dried sample spot is accurately controlled. FIG. 6 shows a graphical representation of a detection characteristic defined as a calibration of a detector signal as a function of analyte content in a sample. Typically, the detector signal is generated by a detector used in or in combination with an analytical measurement system such as a HPLC system or UPLC system. The points along the diagonal dashed line represent the detector response determined in a calibration procedure. Although the detector signal as a function of analyte content is shown as linear, it should be appreciated that for other calibrations the detector signal may exhibit nonlinearity within the calibration range.

The analyte content for a sample measurement can be determined from the detector signal in the calibration range. Ideally, the slope of the detector response should be as large as possible to achieve the greatest measurement sensitivity; however, due to the limited dynamic range of the detector, the analyte content in the measured sample is restricted to a decreasing range of values as the detector sensitivity increases.

If the measurement of the sample results in data that are outside of the calibration range, for example, the measurement point "A" that lies outside the calibration range shown in FIG. 6, sample extraction can be repeated with an increased volume of solvent to reduce the concentration of the analyte and the amplitude of the detector signal. In some instances there may not be an additional dried sample spot available for a subsequent measurement. In particular, if an automated online system is used, the proper concentration range may be required for the original measurement.

Figure 7:
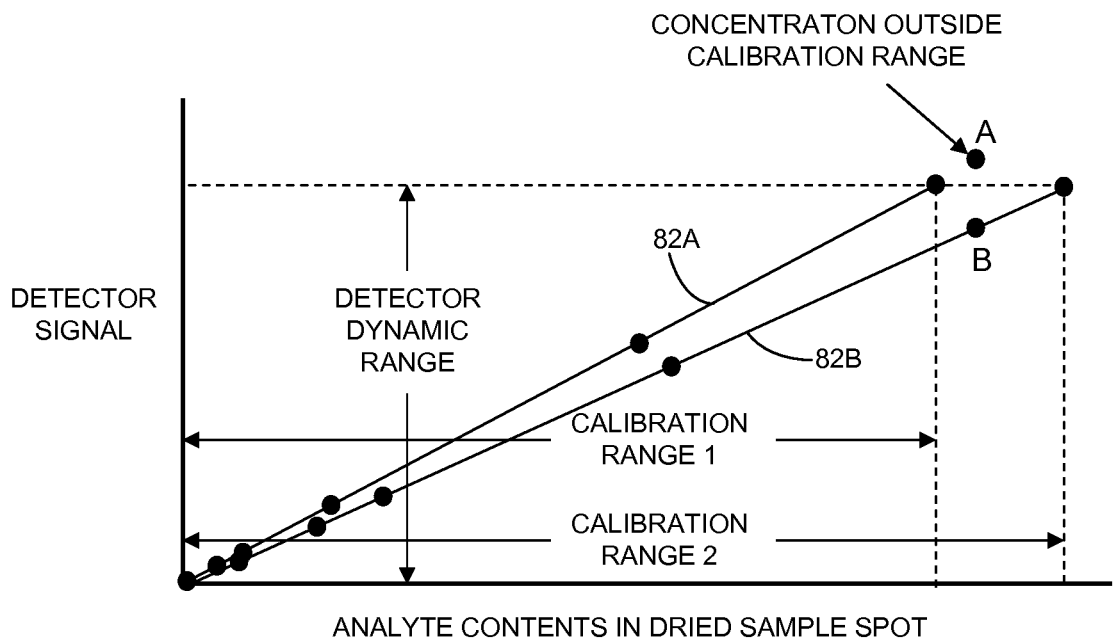
FIG. 7 is a graphical representation of the calibration function of FIG. 6 and a second calibration function that has a lower sensitivity and a greater calibration range.

FIG. 7 shows a first detector response 82A and a second detector response 82B as a function of the amount of analyte in a sample. The first detector response 82A has a greater sensitivity and smaller calibration range compared to the second detector response 82B. In this example, points "A" and "B" represent the same analyte concentration in a dried sample spot; however, point "B" represents a measurement performed with a greater volume of extraction solvent such that the measurement lies within the calibration range of the second detector response 82B.

Figure 8:
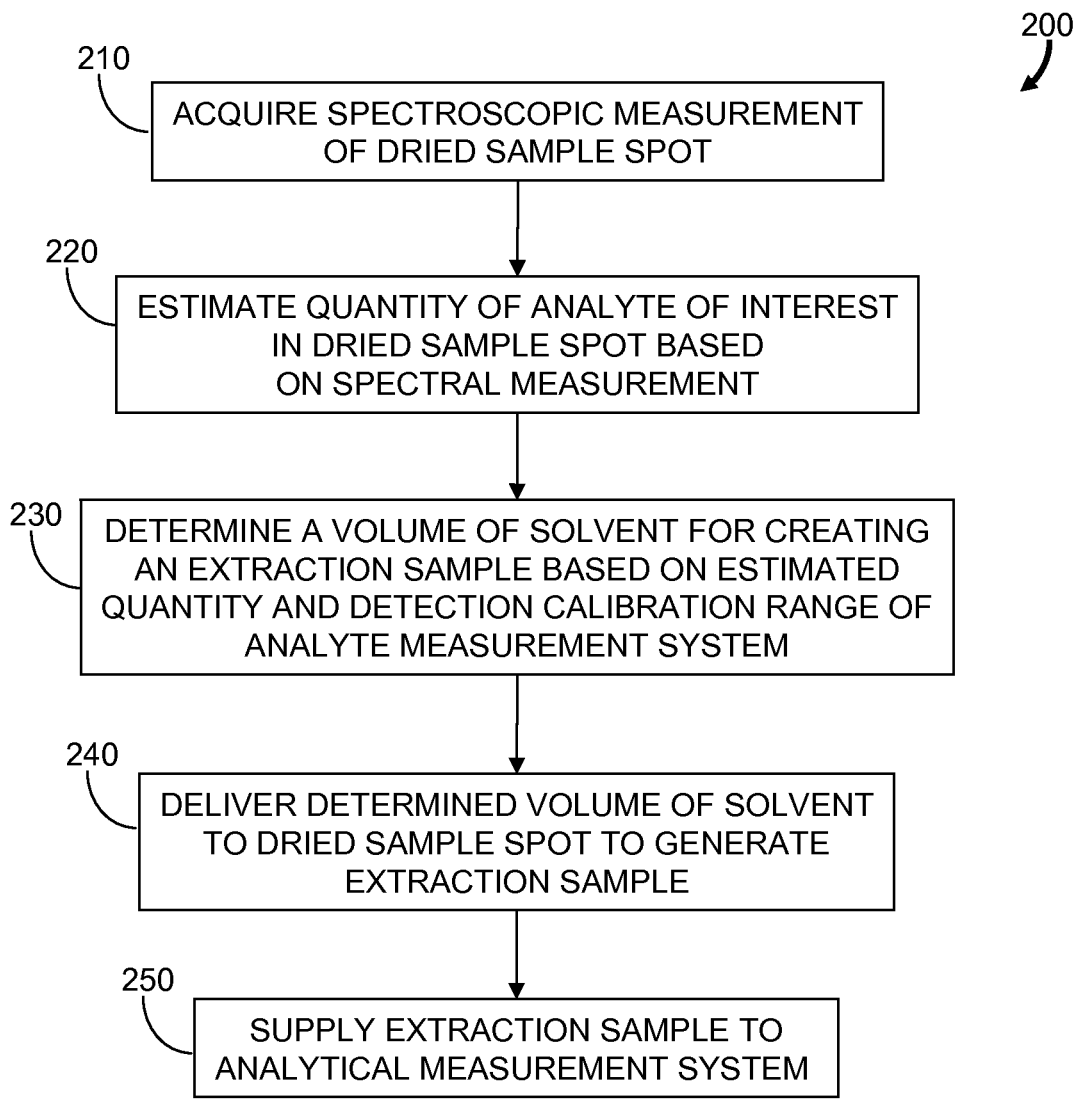
FIG. 8 is a flowchart representation of an embodiment of a method for generating an extraction sample from a dried sample spot according to the invention.

FIG. 8 is a flowchart representation of an embodiment of a method 200 for generating an extraction sample from a dried sample spot. According to the method 200, a spectroscopic measurement of a dried sample spot such as a DBS is acquired (step 210). The spectroscopic measurement enables the quantity of an analyte of interest in the dried sample to be estimated (step 220). A volume of extraction solvent for creating an extraction sample from the dried sample spot is determined (step 230) based on the estimated quantity of the analyte and known detector calibration ranges for an analytical measurement system.

Figure 9:
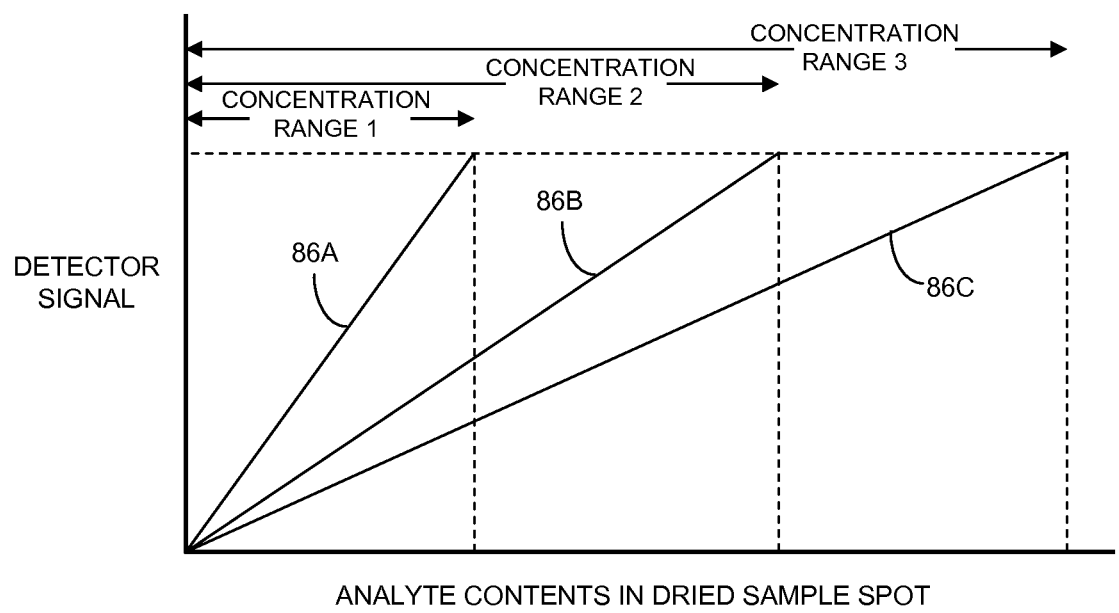
FIG. 9 is a graphical representation of three calibration functions for an analytical measurement system to accommodate low, moderate and high analyte quantities in a sample.

The detection portion of an analytical measurement system (e.g., a HPLC or UPLC system) receiving the extraction sample can have multiple calibration ranges. By way of example, FIG. 9 graphically depicts three detector calibration responses 86A, 86B and 86C for an analytical measurement system that span low, moderate and high analyte quantities, respectively, in the sample. If the spectroscopic measurement yields a low estimated concentration of the analyte in the dried sample spot, the volume of solvent is determined such that the analytical measurement will be performed with the highest sensitivity using calibration range 1. Conversely, if the spectroscopic measurement indicates a high estimated concentration of the analyte, the volume of solvent used to create the extraction sample from the dried sample spot will be higher such that the analytical measurement will be performed with the lowest sensitivity in calibration range 3.

Referring again to FIG. 8, the determined volume of solvent is delivered (step 240) to the dried sample spot to generate the extraction sample. The extraction sample is subsequently provided (step 250) to the analytical measurement system for an accurate measurement of the analyte content.

While the invention has been shown and described with reference to specific embodiments, it should be understood by those skilled in the art that various changes in form and detail may be made therein without departing from the spirit and scope of the invention as recited in the accompanying claims. By way of examples, in embodiments of methods and systems described above, a solvent is used to extract components from a DBS or other form of sample. Generally, the extraction solvent is in the form of a liquid; however, in some embodiments, the extraction solvent may be a gas or a supercritical fluid. In other variations on the embodiments, the sample is provided in a solid form (e.g., a dried tissue sample) instead of a dried sample spot on a carrier. The solid sample does not need to be provided on a carrier and can, in some embodiments, be in a frozen state or be substantially dried. Various aspects of the methods are unchanged, such as acquiring a spectroscopic image of an analyte in the solid sample, determining an extraction region for extraction and generating an extraction sample from the determined region.

What is claimed is:

1. A method of generating an extraction sample from a dried sample spot, the method comprising:
    acquiring a spectroscopic image of an analyte in a dried sample spot, the spectroscopic image comprising spectroscopic data that are dependent on location within the dried sample spot based on a concentration of the analyte according to location within the dried sample spot;
    determining a region of the dried sample spot for extraction based upon the spectroscopic image; and
    generating an extraction sample from the determined region of the dried sample spot.

2. The method of claim 1 wherein the spectroscopic image is a Raman spectroscopy image.

3. The method of claim 1 wherein the dried sample spot is disposed on a sample carrier.

4. The method of claim 3 wherein the sample carrier is a dried blood spot collection card.

5. The method of claim 1 wherein the determination of a region of the dried sample spot for extraction is based on a predetermined aperture.

6. The method of claim 5 wherein the predetermined aperture is based on a diameter of at least one of an outlet port of a supply conduit and an inlet port of an extraction conduit used to supply an extraction solvent to the dried sample spot and to conduct the extraction solvent from the dried sample spot, respectively.

7. The method of claim 5 wherein determining a region of the dried sample spot for extraction comprises selecting the region to maximize an amount of the analyte in the predetermined aperture.

8. The method of claim 5 wherein determining a region of the dried sample spot for extraction comprises selection the region to minimize a spatial variation in a concentration of the analyte in the predetermined aperture.

9. The method of claim 3 wherein generating the extraction sample comprises supplying an extraction solvent to the sample carrier at the determined region of the dried sample spot.

10. The method of claim 9 wherein the extraction solvent passes through the sample carrier at the determined region of the dried sample spot.

11. The method of claim 9 wherein the extraction solvent comprises one of a liquid, a gas and a supercritical fluid.

12. The method of claim 9 further comprising supplying the extraction sample to an analytical measurement system to perform a measurement of the analyte.

13. The method of claim 3 wherein generating the extraction sample comprises separating a portion of the sample carrier having the determined region of the dried sample spot from a remainder of the sample carrier.

14. The method of claim 1 wherein the dried sample spot is one of a dried blood spot, a dried urine spot, a dried saliva spot, a dried plasma spot, a dried serum spot and a dried cerebrospinal fluid spot.

15. A method of generating an extraction sample from a solid sample, the method comprising:
acquiring a spectroscopic image of an analyte in a solid sample, the spectroscopic image comprising spectroscopic data that are dependent on location on the solid sample based on a concentration of the analyte according to location on the solid sample;
determining a region of the solid sample for extraction based upon the spectroscopic image; and
generating an extraction sample from the determined region of the solid sample.

16. The method of claim 15 wherein the solid sample is in a frozen state.

17. The method of claim 15 wherein the solid sample is a dried sample.

18. The method of claim 15 wherein the spectroscopic image is a Raman spectroscopy image.

19. The method of claim 15 wherein generating the extraction sample comprises supplying an extraction solvent to the determined region of the solid sample.

20. The method of claim 19 wherein the extraction solvent comprises one of a liquid, a gas and a supercritical fluid.

21. The method of claim 19 further comprising supplying the extraction sample to an analytical measurement system to perform a measurement of the analyte.

22. The method of claim 15 wherein the determination of a region of the solid sample for extraction is based on a predetermined aperture.

23. The method of claim 22 wherein the predetermined aperture is based on a diameter of at least one of an outlet port of a supply conduit and an inlet port of an extraction conduit used to supply an extraction solvent to the solid sample and to conduct the extraction solvent from the solid sample, respectively.

24. The method of claim 22 wherein determining a region of the solid sample for extraction comprises selecting the region to maximize an amount of the analyte in the predetermined aperture.

25. The method of claim 22 wherein determining a region of the solid sample for extraction comprises selection the region to minimize a spatial variation in a concentration of the analyte in the predetermined aperture.

26. The method of claim 15 wherein generating the extraction sample comprises separating a portion of the solid sample defined by the determined region from a remainder of the solid sample.

* * * * *